(12) United States Patent
Lanzalotti

(10) Patent No.: US 8,090,591 B2
(45) Date of Patent: Jan. 3, 2012

(54) HEALTH CARE FINANCING

(76) Inventor: John A. Lanzalotti, Williamsburg, VA (US)

( * ) Notice: Subject to any disclaimer, the term of this patent is extended or adjusted under 35 U.S.C. 154(b) by 1275 days.

(21) Appl. No.: 11/518,432

(22) Filed: Sep. 11, 2006

(65) Prior Publication Data

US 2007/0061172 A1   Mar. 15, 2007

Related U.S. Application Data

(60) Provisional application No. 60/715,569, filed on Sep. 12, 2005.

(51) Int. Cl.
*G06Q 50/00* (2006.01)
(52) U.S. Cl. .......................................................... 705/2
(58) Field of Classification Search ..................... 705/2
See application file for complete search history.

(56) References Cited

U.S. PATENT DOCUMENTS

| | | | |
|---|---|---|---|
| 5,644,778 A * | 7/1997 | Burks et al. | 705/2 |
| 7,617,114 B1 * | 11/2009 | Tooke et al. | 705/2 |
| 2006/0080144 A1 * | 4/2006 | Goel et al. | 705/2 |
| 2006/0149595 A1 * | 7/2006 | Williams et al. | 705/2 |
| 2007/0050205 A1 * | 3/2007 | Lieberman | 705/2 |

* cited by examiner

*Primary Examiner* — Gerald J. O'Connor
*Assistant Examiner* — Hiep V Nguyen

(57) ABSTRACT

A health care finance system according to the invention features an expanded health care savings and asset account that may be funded in a variety of ways. An insurance carrier is paid a premium out of the account. When a patient sees a health care provider, the health care provider generates an electronic medical work-up. The work-up is analyzed by software, which determines an appropriate protocol and complexity level associated with the patient's condition. The protocol and complexity level are then transmitted to the insurance carrier, and the insurance carrier makes a global payment directly into the patient's health care asset account based on the determined protocol and complexity level. The patient accesses those funds directly, e.g., using an electronic debit card, to pay the health care provider.

4 Claims, 4 Drawing Sheets

HEALTH CARE FINANCING

CROSS-REFERENCE TO RELATED APPLICATIONS

This application claims the priority benefit of provisional application 60/715,569 filed Sep. 12, 2005, the contents of which are incorporated by reference in their entirety.

BACKGROUND AND FIELD OF THE INVENTION

Health Care costs and prices are increasing. This inflation is a function of insurance design and the current method of filing claims by providers, third party payment and third party regulation. Currently, the methods to finance health care are complex, inefficient, and poorly designed. In particular, there are a lack of proper incentives, many perverse incentives, increasing micromanagement, overhead and administration costs of medical care delivery, all resulting in a dysfunctional market characterized by high costs, high prices, and low quality of insurance and health care delivery. As system specifications and the need to micromanage the finance and delivery of healthcare to control rising costs, the task of configuring a system has become more highly complex, further driving up costs. This increased complexity has resulted in a need to shift the paradigm of the design of health care insurance, and the finance and delivery of health care; and created a need for a computer based system to obviate the inefficiencies of the current system and handle complicated data that is necessary to determine the proper insurance payment for any given patient with their individual needs.

SUMMARY OF THE INVENTION

A health care finance system according to the invention features an expanded health care savings and asset account that may be funded in a variety of ways. An insurance carrier is paid a premium out of the account. When a patient sees a health care provider, the health care provider generates an electronic medical work-up. The work-up is analyzed by software, which determines an appropriate protocol and complexity level associated with the patient's condition. The protocol and complexity level are then transmitted to the insurance carrier, and the insurance carrier makes a global payment directly into the patient's health care asset account based on the determined protocol and complexity level. The patient accesses those funds using an electronic debit card, to pay the health care provider directly.

It is important to note that the terms "protocol" and "complexity level" have specific meanings unique to this invention. The term "protocol" means a diagnosis or condition representing the primary morbidity for which the patient is insured. The term "complexity level" represents increasing morbidity and its treatment associated with the insurable event and the presence or absence of any co-morbidity and its treatment associated within that particular protocol.

The purpose of this invention is to redesign health insurance to eliminate many of the perverse incentives and inefficiencies of the current health insurance product and in so doing eliminate twenty-two of the twenty-three cost drivers—those problems associated with current health insurance design that are responsible for driving up the costs of health care in this country (that consequently drives up the costs of all of our goods and services manufactured or produced by American business)—that are responsible for the inflated cost and prices of today's health care.

The entire system and all of the software that comprises this invention is an interdependent functional unit. Each component of this invention has been designed to create proper incentives for all players in the health care market place that will lower costs, provide proper checks and balances, and create a level playing field with affordable, portable health insurance for all Americans in a functional health care market.

This invention will allow the doctor freedom to practice medicine, i.e., to diagnose and treat the patient within the context of appropriate care to offer the best care at the lowest prices to his patient and not be restricted and constrained by the overweening top-down bureaucratic control necessary with today's insurance design. It also allows the insurance payment to be closely matched to any patient's particular medical needs and eliminates the need for third-party rationing of health care to the patient.

BRIEF DESCRIPTION OF THE DRAWINGS

The invention will now be described in greater detail in connection with the Figures, in which.

DETAILED DESCRIPTION OF EMBODIMENTS OF THE INVENTION

Figure 1:
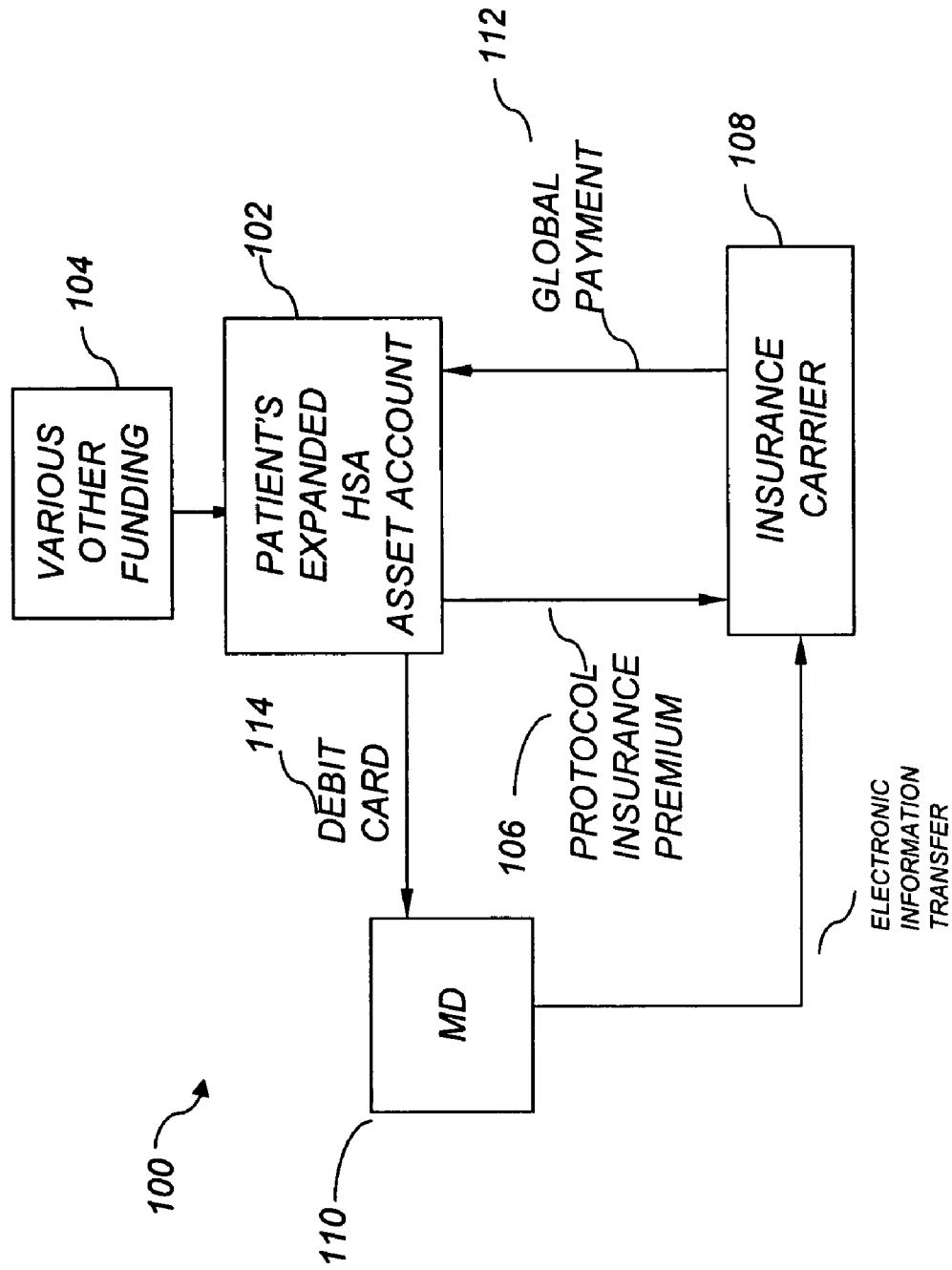
FIGS. 1 and 2 are flow diagrams illustrating the computerized operation of a health care finance system according to the invention.

A system 100 for financing and delivering health care according to the invention is illustrated in FIG. 1. According to the inventive system 100, an expanded personal and portable tax-free health care savings and asset account (EHSA) 102 is established for every American individual or family using annual funding 104 from a variety of sources. These sources can include defined contributions from an employer; contributions from the owner of the account; tax credits; transfer payments from Medicaid or Medicare; E.I.T.C. funds; federal tax withholding from the working poor; charity; etc.

Twenty-five to thirty percent of the annual funding of the asset account 102 is used by the patient to pay an annual premium 106 for "protocol insurance" to any insurance carrier 108. The remainder of the funding rolls over from year to year and grows tax-free and can be used for discretionary and initial visit (any diagnostic procedures done before any determination has been made by the doctor concerning diagnosis) health care spending, as well as retirement income by the beneficiaries of the account 102.

When a patient sees a doctor or other health care provider 110, the doctor or health care provider examines the patient and prepares a computerized medical workup which will be used to determine a dollar amount to be paid directly and electronically into the patient's EHSA by the insurance carrier 108. Software that is part of this invention evaluates the work-up and determines information about which established "protocol" and "complexity level" the patient's condition corresponds to, as described in greater detail below. An electronic transfer of this information from the provider's office computer to the insurance carrier's computer triggers a "global payment" 112 from the insurance carrier into the patient's EHSA 112. The global payment provides the patient with enough money to be able to pay for all anticipated expenses (at fair market value) associated with treatment, e.g., doctor bills, hospital bills, pharmaceutical bills, surgery bills, and bills for any other necessary therapy. The global payment made is determined by protocol and complexity level and course of treatment for a given condition. This insurance payment does not require a co-payment or deductible payment from the patient. The patient then accesses this global payment in his EHSA 102 with a medical debit card 114 to pay for all health care goods and services required to treat the condition.

Figure 2:
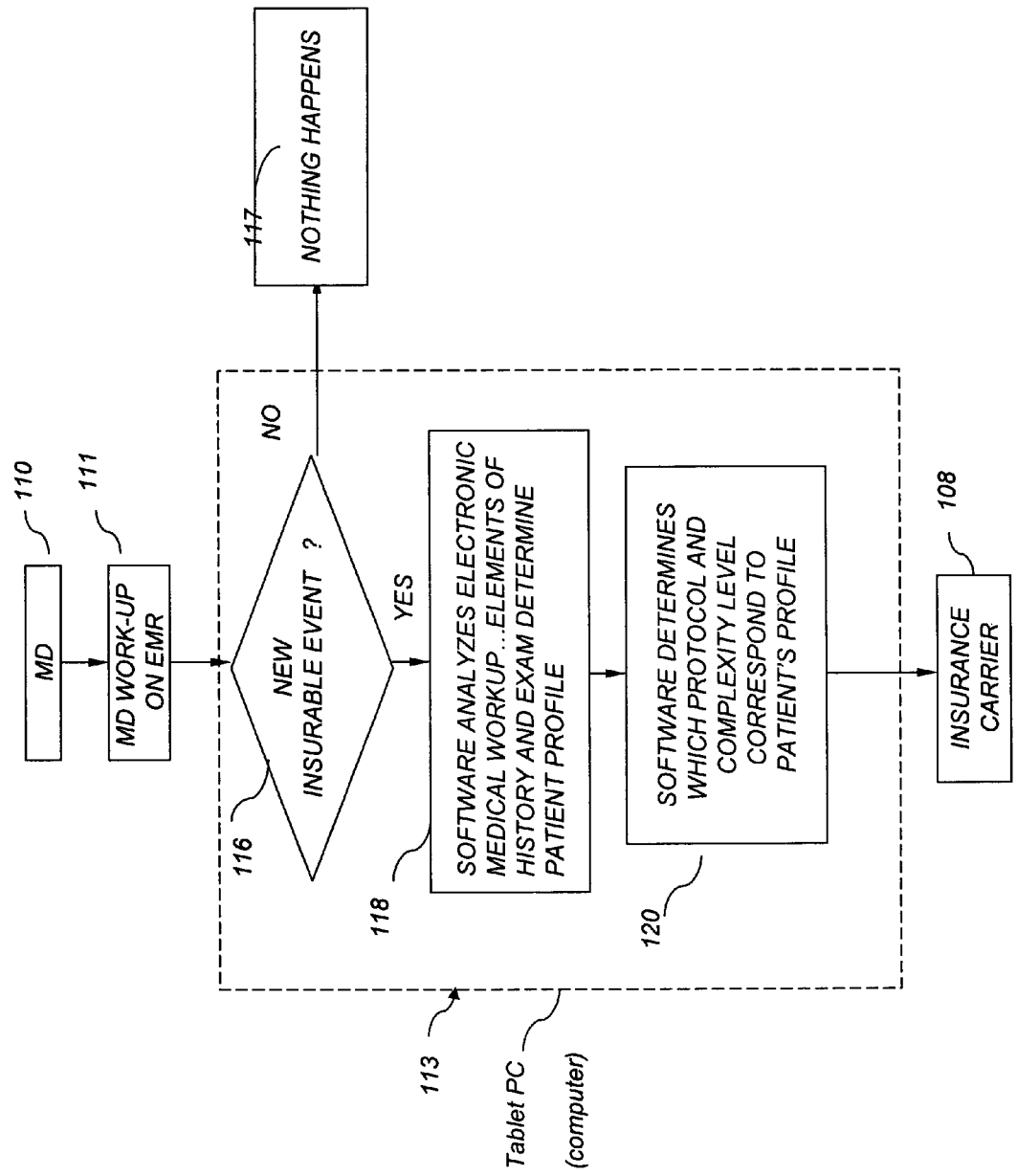

Creation of an electronic medical record (EMR) and analysis of that record, as well as determination of protocol and complexity level, is illustrated in more detail in FIG. 2. As illustrated, the physician or other health care provider 110 does a medical work-up on a computer 113, thus creating an electronic medical record 111, using drop-down menus to select appropriate and thorough descriptions of the patient's medical history, physical exam, lab and imaging results, and the physician's diagnosis and treatment plan. Software that is part of this invention interacts with the software program used to create the work-up and analyzes this work-up and determines if there is a "new insurable event" 116. (An insurable event 116 is a medical diagnosis or condition that is contracted by the insurance company to be paid when that event occurs.) If there is not a new insurable event, nothing happens 117 and the patient is responsible for paying the bill for that day's service (e.g., out of non-insurance-derived funds from the EHSA in pre-tax dollars (money that remains in the account after the annual insurance premium is paid), (not out of pocket in post tax dollars as is done in the current system of insurance). If, on the other hand, there is a new insurable event, the software determines the patient's medical profile from informational elements representing aspects of the patient's history; exam, lab, and imaging results; physician's diagnosis and plan of treatment; etc. in the electronic medical patient record 118. The software then determines which established protocol and complexity level the patient's profile corresponds to, e.g., by using matching algorithms. The software then transfers information concerning the patient's protocol and complexity level to the insurance carrier 108, which triggers global payment into the EHSA as explained above. This is analogous to and replaces filing an insurance claim as in the current system.

Figure 3:
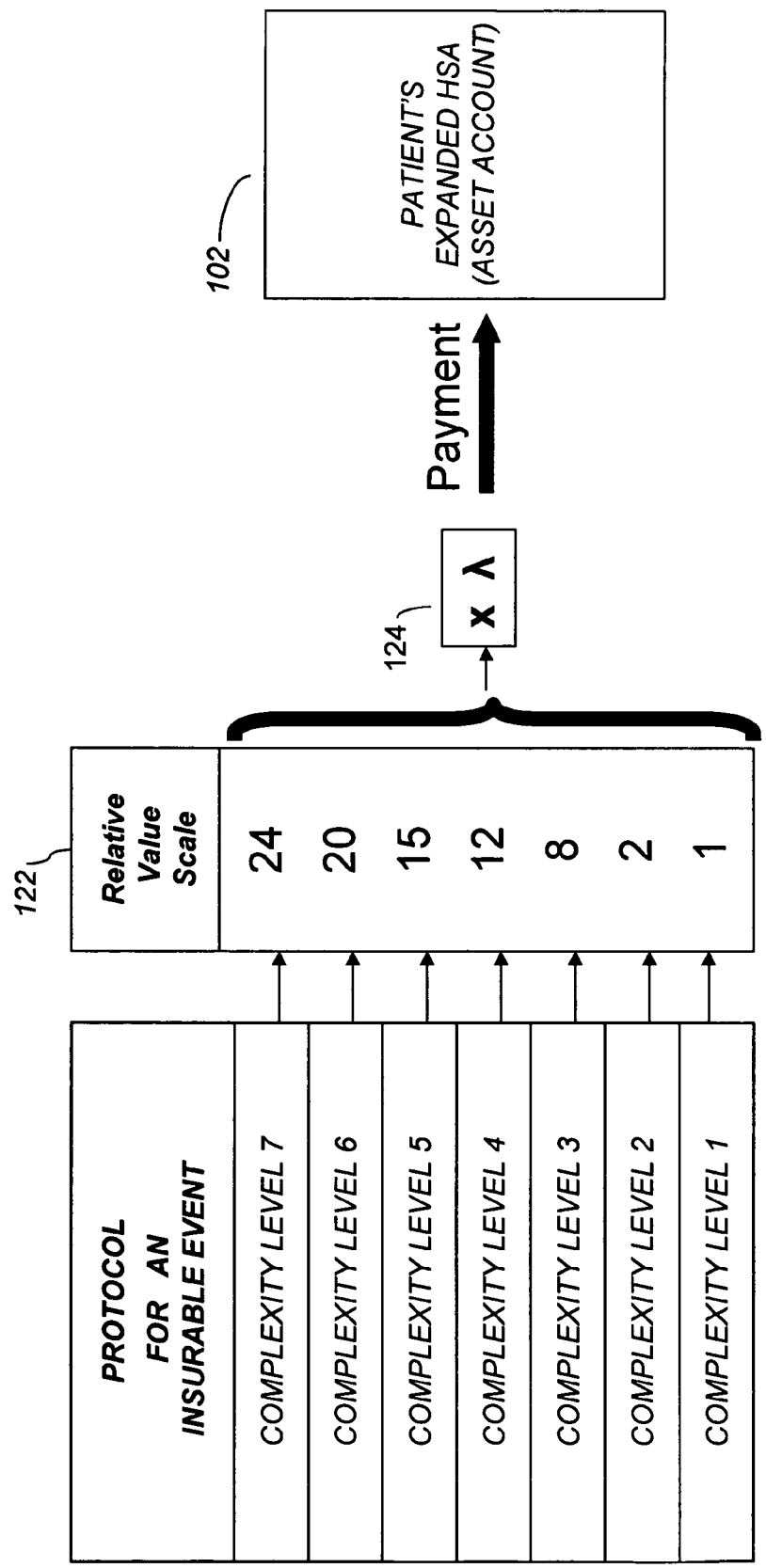
FIG. 3 is a diagram illustrating the interrelationship between protocol and complexity level and the amount of global payment made into a patient's health care savings and asset account.

As noted above, the amount of the global payment for each insurable event is a function of or determined by the complexity level and protocol thereof, as illustrated in FIG. 3. Each established protocol (a diagnosis or condition representing the primary morbidity) in the software is comprised of several complexity levels. Each complexity level represents increasing morbidity associated with the insurable event and the presence or absence of any co-morbidity associated with that particular protocol. Each complexity level is associated with a relative value scale number 122, which represents the relative value of each level of necessary care. (FIG. 3 shows seven complexity levels, but in reality the number of complexity levels may vary and depends on the particular diagnosis). In other words, the sicker the patient, the more money the patient will need to pay his medical bills. Because health care is primarily a local market phenomenon, the relative value scale number is then multiplied 124 by a factor λ that floats with known local market-related components to determine the actual dollar amount to be transferred as a global payment 112 into the patient's EHSA 102.

By way of example, a patient diagnosed with acute gall bladder disease due to gall stones would correspond to a protocol for cholelithiasis. Complexity level 1, for example, would be a single large gall stone with only occasional discomfort. The complexity level would pay for the doctor's visits to diagnose and treat the problem, the imaging to diagnose the problem, and the medication to control the occasional discomfort. A higher complexity level would pay enough to diagnose and treat the problem if, for example, the patient had multiple small stones, was diabetic, and had chronic obstructive pulmonary disease. In that case, the patient would need money for the doctor visits to diagnose, treat, and follow up from an in-hospital stay during which the patient would have surgery to remove the gallbladder, medicine for infection and pain and intensive pulmonary therapy to prevent and treat atelectasis following surgery.

Figure 4:
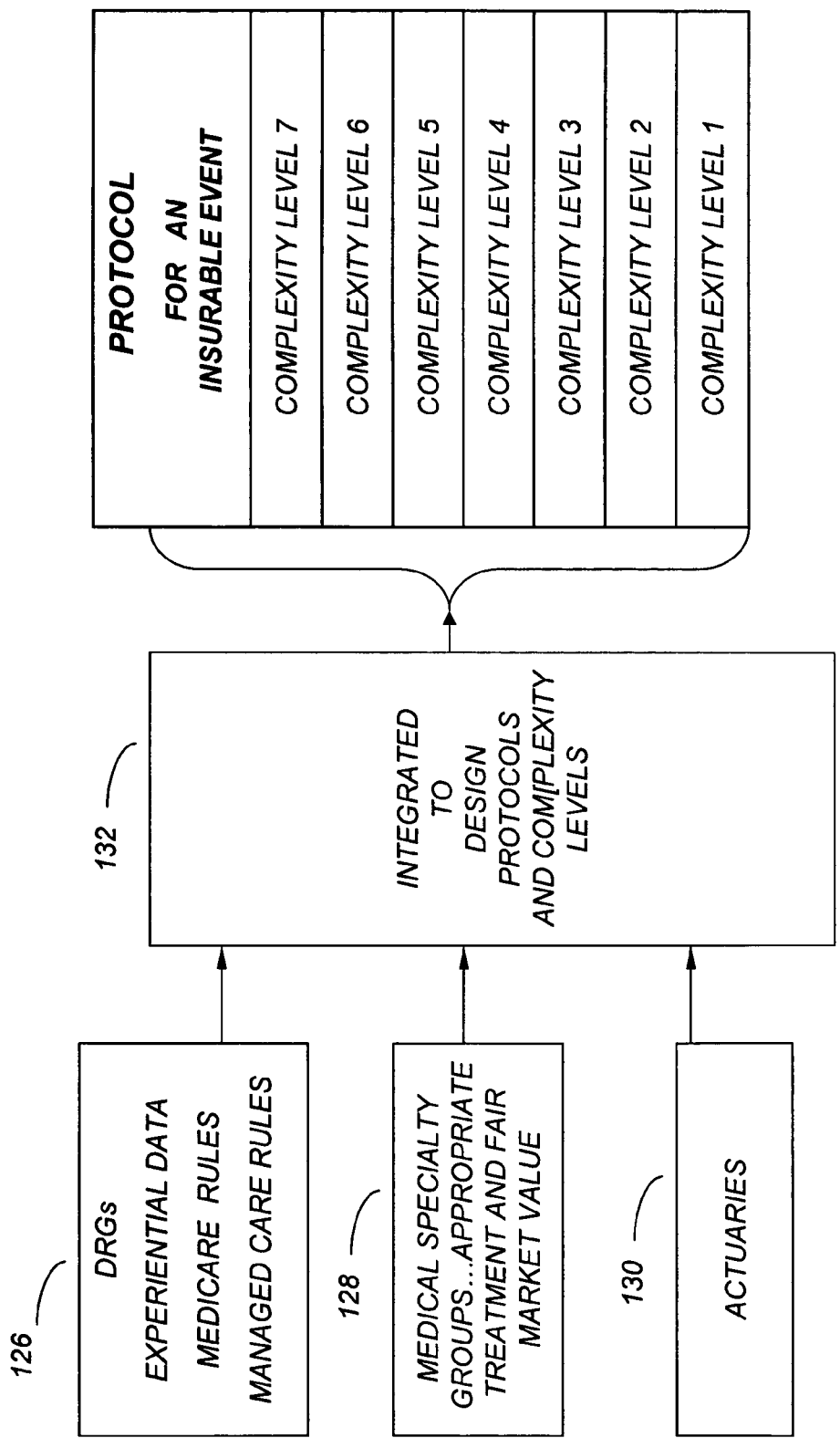
FIG. 4 is a diagram illustrating the original establishment of protocols and complexity levels.

FIG. 4 illustrates how the protocols and complexity levels are originally set up according to the invention. Existing data concerning health care finance and delivery, outcomes, diagnostic related groups (DRGs), and all Medicare and managed care rules as well as empirical and experiential data from the past thirty years of medical practice 126 is gathered and analyzed by a team of physicians from the various medical specialty groups. They will analyze this data in terms of appropriate treatment and fair market value for all diagnostic and treatment procedures 128. More specifically, selected doctors from each of the medical specialties societies will construct the complexity levels by using the data to determine appropriate treatment for a given set of diagnostic signs and symptoms, laboratory and imaging parameters, severity of the primary morbidity and the presence or absence of co-morbidities, etc. In addition, the doctors will determine appropriate fair market value for all doctor visits, lengths of hospital stays, appropriate medication, specialty consultations, surgeries, and other therapies. This information is then specifically integrated into the complexity levels of each individual protocol. This integrated data is then subjected to an actuarial analysis 130, which will determine the relative value of the payments assigned to each complexity level as well as the dollar amounts to be paid.

It will be appreciated that the foregoing description of an embodiment of the invention is for illustrative purposes only and that various modifications to and departures from the disclosed embodiment will occur to those having skill in the art. Accordingly, what is deemed to be the invention is defined by the following claims.

I claim:

1. A health care financing method comprising:
initially developing and calculating an insurance payment protocol using a computer system, wherein the insurance payment protocol comprises a plurality of complexity levels,
wherein each complexity level represents a manifestation of:
a respective morbidity for a clinical presentation, and
a respective treatment associated with said respective morbidity,
wherein each complexity level comprises quantified, historical, health care cost data based on an analyses by physicians of:
health care finance and delivery data for each respective morbidity and each respective treatment,
if applicable, at least one historical patient outcome for the each respective morbidity and each respective treatment, and
historic diagnostic related group data for each respective morbidity and each respective treatment, a quantified compliance value of at least one historical cost for compliance with at least one of government regulations and health care managed care rules, and quantifying experiential health care value associated with empirical and historical experimental data for each respective morbidity and each respective treatment;

wherein each complexity level is assigned an indexed relative value by physicians, the initial indexed relative value based on:

an analysis of each element analyzed above, an assignment to each complexity level, morbidity and treatment information of similar value so that in the aggregate, all complexity levels within a protocol will accommodate all possible clinical presentations of the morbidity and all possible treatments of that morbidity, an assignment by the doctors, developing the initial protocol, of an initial value representing a reasonable amount enough to cover all costs for an episode of care related to the complexity level for that morbidity and treatment selected by the physician and provide a profit of a least 10%, further adjusting each complexity level of the insurance payment protocol by a local, geographic market factor actuarially balanced against an insurance premium;

quantifying a global payment for a patient by matching the complexity level of the adjusted insurance payment protocol with unique patient medical condition data, wherein the patient medical condition data comprises:

clinical data comprising all associated medical condition manifestations, and selected treatment requirements, the selected treatment requirements identified to treat an entire episode of care by a patient's health care provider and a patient, and wherein the global payment comprises a lump sum payment to pay for all necessary and essential health care at full, fair market value, the necessary and essential health care arising from the patient medical condition data and representing the selected treatment requirements; and transferring the global payment to a financial fiduciary health savings asset account for the patient, the financial fiduciary health savings asset account comprising one or more global payments.

2. The method of claim 1 wherein the fiduciary health savings account further comprises non-taxable insurance derived funds and non-taxable, non-insurance derived funds to benefit the patient to pay for all necessary and essential care.

3. The method of claim 1, further comprising:

analyzing a cost of one health care treatment of the comprehensive health care treatment, the cost associated a health care provider;

selecting a health care provider to provide the one health care treatment; and authorizing to transfer a portion of the global payment from the health savings account to a health care provider's asset account to pay for the one health care treatment.

4. A health care financing system comprising:

an established, quantified protocol and complexity level computer database initially developed by physicians:

wherein each complexity level represents a manifestation of:

a respective morbidity for a clinical presentation, and a respective treatment associated with said respective morbidity, wherein each complexity level comprises quantified, historical, health care cost data based on an analyses by physicians of:

health care finance and delivery data for each respective morbidity and each respective treatment, if applicable, at least one historical patient outcome for the each respective morbidity and each respective treatment, and historic diagnostic related group data for each respective morbidity and each respective treatment, a quantified compliance value of at least one historical cost for compliance with at least one of government regulations and health care managed care rules, and a quantified experiential health care value associated with empirical and historical experimental data for each respective morbidity and each respective treatment;

wherein the value of each complexity level is adjusted at least annually by the market and balanced against actuarial date in order to keep insurance premiums reasonably low to make health insurance accessible a network connecting a communications device of a healthcare provider and a communications device of a patient with the protocol and complexity computer database of the insurer; and the healthcare provider communications device capable of performing the steps of:

matching unique patient medical condition data with protocol and complexity data to determine if there is a new insurable event, wherein the patient medical condition data comprises:

clinical data comprising all associated medical condition manifestations, and selected treatment requirements, the selected treatment requirements identified to treat an entire episode of care by a patient's health care provider and a patient, and wherein the global payment comprises a lump sum payment to pay for all necessary and essential health care at full, fair market value, the necessary and essential health care arising from the patient medical condition data and representing the selected treatment requirements;

if there is a new insurable event, adjusting the insurance payment protocol by a local, geographic market factor; and transferring the global payment to a financial fiduciary health savings asset account for the patient, the financial fiduciary health savings asset account comprising one or more global payments.

* * * * *